(12) United States Patent
Cefai et al.

(10) Patent No.: US 10,391,237 B2
(45) Date of Patent: Aug. 27, 2019

(54) ACTUATOR AND ACTUATION METHOD

(71) Applicant: CELLNOVO LTD, Swansea (GB)

(72) Inventors: Joseph Cefai, Swansea (GB); Julian Shapley, Swansea (GB); Matthew Powell, Swansea (GB)

(73) Assignee: CELLNOVO LIMITED, Swansea (GB)

( * ) Notice: Subject to any disclaimer, the term of this patent is extended or adjusted under 35 U.S.C. 154(b) by 379 days.

(21) Appl. No.: 15/114,842

(22) PCT Filed: Jan. 30, 2015

(86) PCT No.: PCT/GB2015/050252
§ 371 (c)(1),
(2) Date: Jul. 27, 2016

(87) PCT Pub. No.: WO2015/114374
PCT Pub. Date: Aug. 6, 2015

(65) Prior Publication Data
US 2016/0346456 A1  Dec. 1, 2016

(30) Foreign Application Priority Data

Jan. 30, 2014 (GB) .................................. 1401586.1

(51) Int. Cl.
*A61M 5/142* (2006.01)
*F04B 43/04* (2006.01)
(Continued)

(52) U.S. Cl.
CPC ........ *A61M 5/142* (2013.01); *A61M 5/14224* (2013.01); *A61M 5/14244* (2013.01);
(Continued)

(58) Field of Classification Search
CPC ...... A61M 5/14224; A61M 2205/3673; A61M 2205/0272; A61M 2205/0277;
(Continued)

(56) References Cited

U.S. PATENT DOCUMENTS

| 5,020,325 A | 6/1991 | Henault |
| 2004/0094733 A1 | 5/2004 | Hower et al. |

(Continued)

FOREIGN PATENT DOCUMENTS

| GB | 2443261 | 4/2008 |
| GB | 1401586.1 | 1/2014 |

OTHER PUBLICATIONS

U.K. Intellectual Property Office, GB Application No. GB 1401586.1, "Search Report under Section 17(5)" dated Sep. 4, 2015, 5 pages.
European Patent Office, "Notification of Transmittal of the ISR and the Written Opinion of the International Searching Authority, or the Declaration," in PCT Application No. PCT/GB2015/050252, dated Jun. 11, 2015, 14 pages.

*Primary Examiner* — Nathan R Price
*Assistant Examiner* — Anh Bui
(74) *Attorney, Agent, or Firm* — Kang S. Lim

(57) ABSTRACT

An actuator comprises: a cavity containing a working medium (B) that reversibly expands as it undergoes a phase change from a solid to a liquid state; a diaphragm disposed adjacent the cavity such that expansion and contraction of the expandable working medium (B) causes the diaphragm to deflect, and a semiconductor element (A) disposed in the cavity. The semiconductor element (A) is operable in a first mode to heat the working medium (B) to cause it to undergo the phase change into the liquid state, and is operable in a second mode to measure the temperature at the semiconductor element (A). The corresponding actuation method is also disclosed.

18 Claims, 11 Drawing Sheets

(51) Int. Cl.
    *F04B 43/06* (2006.01)
    *F04B 49/06* (2006.01)
    *F03G 7/06* (2006.01)
    *A61M 5/162* (2006.01)
    *A61M 5/172* (2006.01)

(52) U.S. Cl.
    CPC .......... *A61M 5/162* (2013.01); *A61M 5/1723* (2013.01); *F03G 7/06* (2013.01); *F04B 43/043* (2013.01); *F04B 43/06* (2013.01); *F04B 49/065* (2013.01); A61M 2205/3337 (2013.01); A61M 2205/3368 (2013.01); A61M 2205/3569 (2013.01); A61M 2205/3584 (2013.01); A61M 2205/3673 (2013.01); A61M 2205/505 (2013.01); A61M 2205/8206 (2013.01); A61M 2205/8237 (2013.01); A61M 2209/086 (2013.01); A61M 2230/005 (2013.01); A61M 2230/201 (2013.01); A61M 2230/63 (2013.01)

(58) Field of Classification Search
    CPC .. A61M 2205/0283; A61M 2205/0288; A61M 2205/0294
    See application file for complete search history.

(56) References Cited

U.S. PATENT DOCUMENTS

| | | |
|---|---|---|
| 2010/0137784 A1 | 6/2010 | Cefai et al. |
| 2010/0145272 A1* | 6/2010 | Cefai ............... F04B 43/043 604/114 |
| 2011/0142688 A1* | 6/2011 | Chappel ............ A61M 5/16854 417/213 |
| 2011/0316562 A1 | 12/2011 | Cefai et al. |

* cited by examiner

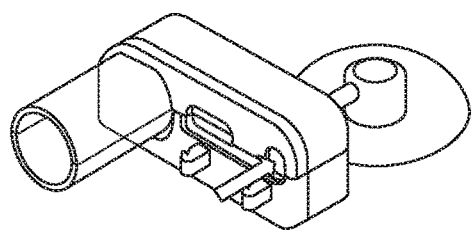
Figure 6A
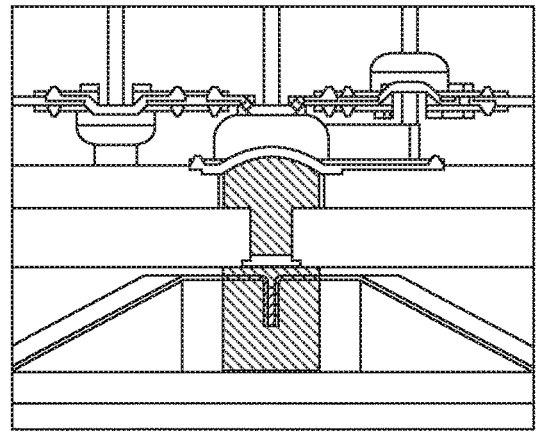
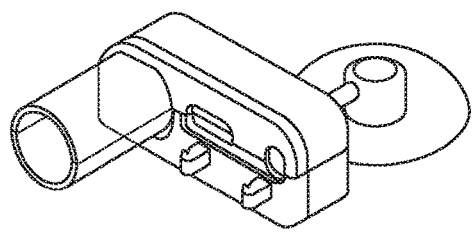
Figure 6B
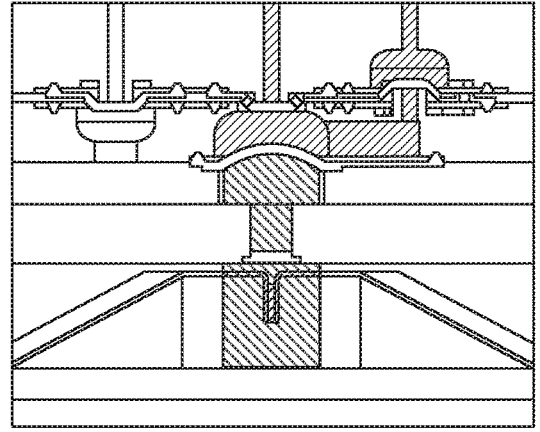
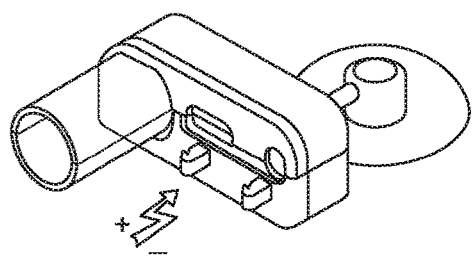
Figure 6C
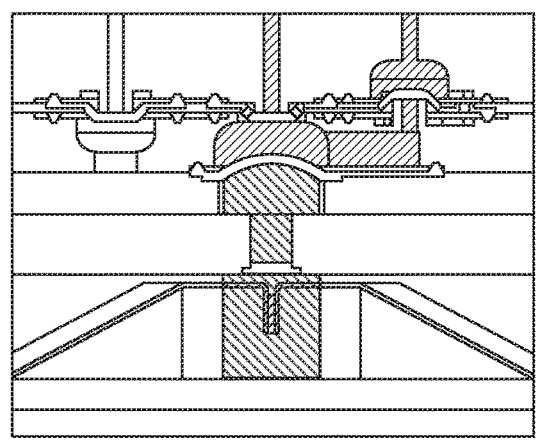

Figure 7A
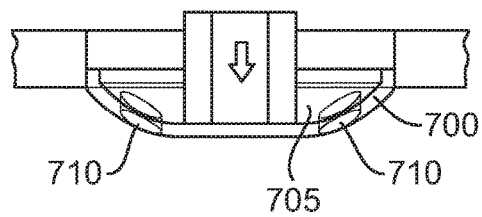
Figure 7B
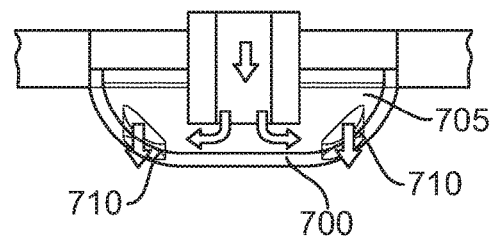
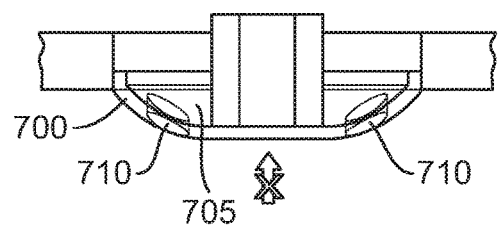
Figure 7C
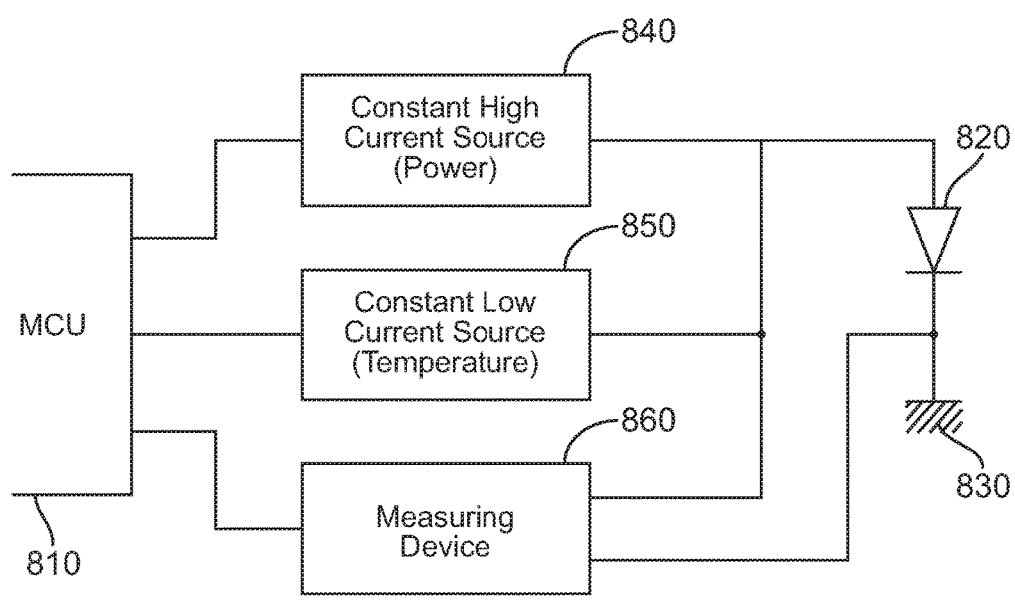
Figure 8

| Temperature | Ontime |
|---|---|
| 6 | 1168 |
| 8 | 1124 |
| 10 | 1080 |
| 12 | 1036 |
| 14 | 992 |
| 16 | 948 |
| 18 | 904 |
| 20 | 860 |
| 22 | 816 |
| 24 | 772 |
| 26 | 728 |
| 28 | 684 |
| 30 | 640 |
| 32 | 596 |
| 34 | 552 |
| 36 | 508 |
| 38 | 464 |
| 40 | 420 |
| 42 | 376 |
| 44 | 332 |
| 46 | 288 |
| 48 | 244 |
| 50 | 200 |

On time (basal) = 1300 - (Measured Temperature *22)

On time (bolus) = 1800 - (Measured Temperature *22)

ACTUATOR AND ACTUATION METHOD

CROSS-REFERENCE TO RELATED APPLICATIONS

The present application is a United States National Stage entry under 35 U.S.C. § 371 of International Application No. PCT/GB2015/050252 filed Jan. 30, 2015, designating the United States of America and published in English on Aug. 6, 2015, which in turn claims priority to Great Britain Application No. 1401586.1, filed Jan. 30, 2014, each of which is incorporated herein by reference in their entirety.

FIELD OF THE INVENTION

The present invention relates to an actuator and an actuation method, preferably for a therapeutic product delivery device.

BACKGROUND TO THE INVENTION

Conventionally, Type 1 diabetes has been treated with daily insulin injections. However, this inevitably results in insulin levels that do not match the normal and rapid changes in blood glucose which occur in a patient throughout the day. On the one hand, insufficient insulin and high glucose levels lead to immediate symptoms and contribute to long-term complications. On the other hand, too much insulin may result in too little blood sugar leading to loss of consciousness and convulsions. As an alternative to injections, insulin pump therapy is intended to mimic the normal physiology of the healthy pancreas. Unlike multiple daily insulin injections, an insulin pump is able to provide a constant background infusion of insulin that can be adjusted according to individual need, compensating for daily activity and exercise routines. The pump may also be programmed to deliver bolus doses of insulin to address the big glucose swings in the blood that would otherwise result from eating and drinking. By mimicking the natural physiology of the pancreas, insulin pump therapy aims to maintain a constantly normal blood glucose level; avoiding the highs that are associated with meals or the lows that come from too much insulin.

One type of insulin pump uses a wax actuator to pump insulin. The wax expands when heated by a diode embedded within the wax. A problem with this technique is that the amount of power required to pump a given quantity of insulin varies dramatically in dependence on the starting temperature of the wax at the time power is supplied to the diode, making it difficult to deliver precise amounts of insulin to a patient.

SUMMARY OF THE INVENTION

According to an aspect of the present invention, there is provided an actuator, comprising:
a cavity containing a working medium that reversibly expands as it undergoes a phase change from a solid to a liquid state;
a diaphragm disposed adjacent the cavity such that expansion and contraction of the expandable working medium causes the diaphragm to deflect;
a semiconductor element disposed in the cavity, wherein the semiconductor element is operable in a first mode to heat the working medium to cause it to undergo the phase change into the liquid state, and is operable in a second mode to measure the temperature at the semiconductor element.

By using the same semiconductor element for both heating and temperature detection, the temperature is measured at exactly the right location. Moreover, there is no need to provide a separate temperature sending element. It will be appreciated that this is only possible because it is not necessary to know the temperature at the time a pulse of electrical power is applied to the semiconductor element. It is only necessary to know the temperature at the semiconductor element just before a pulse is to be started (basal mode), or after the pulse has completed (bolus mode). Preferably, the semiconductor element is a diode.

In one embodiment, in the first mode, a first constant current is applied across the semiconductor element to heat the working medium. In the second mode, a second constant current lower than the first constant current is applied across the semiconductor element, a voltage drop across the semiconductor element is measured, and the voltage drop is used to infer the temperature at the semiconductor element.

The actuator may comprise control circuitry for setting a pulse start time and a pulse duration for applying an electric current to the semiconductor element, at least one of the pulse start time and pulse duration being set in dependence on the temperature measured by the semiconductor element. It will be appreciated that there are advantages associated with setting the pulse start time and/or pulse duration in dependence on temperature even where the semiconductor element only performs heating and does not perform temperature sensing (i.e. where the temperature sensing is performed by another element). Preferably, the deflection of the diaphragm is used to pump a therapeutic product to a patient.

Preferably, in a basal delivery mode, the control circuitry is operable to set the pulse duration in dependence on the temperature measured by the semiconductor element just before the pulse is due to be started. This enables the pulse duration to be set to achieve the accurate delivery of a quantity of insulin, since temperature variation can be discounted.

Preferably, in a bolus delivery mode, the control circuitry is operable to trigger the start of a new pulse when the temperature measured by the semiconductor element has dropped to a predetermined temperature following the end of the previous pulse. This enables each new pulse to be started as soon as the wax has cooled enough for the position of the actuator to be reset, permitting delivery of the bolus dose as quickly as possible. Also, the amount of energy required to deliver the dose is lower, since less energy is required per pulse to raise the temperature from the predetermined temperature than would be the case to raise the temperature from the ambient temperature. In this case, the pulse duration of each new pulse is set in dependence on the predetermined temperature.

Preferably, in the basal delivery mode, the control circuitry is operable to control the rate of delivery of the therapeutic product by setting the frequency with which pulses of electric current are applied to the semiconductor element.

Preferably, in the basal delivery mode, the control circuitry is operable to monitor an amount of therapeutic product delivered over the previous n pulses, wherein n is an integer value greater than zero, and to modify a pulse parameter in relation to the next one or more pulses in dependence on a difference between an intended delivery quantity and an actual delivery quantity over those n pulses. The pulse parameter may be an interval between successive pulses. Preferably however, the pulse parameter is the duration of the next one or more pulses. This provides a simple and effective correction technique, without increasing the complexity of scheduling by adding in additional pulses or moving existing planned pulses.

Preferably, if the actual delivery quantity is less than the intended delivery quantity then the duration of the next pulse is increased by an amount which is dependent on the magnitude of the difference, and if the actual delivery quantity is more than the intended delivery quantity then the duration of the next pulse is decreased by an amount which is dependent on the magnitude of the difference.

Preferably, in the bolus delivery mode, the control circuitry is operable to deliver a predetermined bolus dose by calculating a first schedule of successive pulses required to deliver a first portion of the predetermined bolus dose, applying the calculated first schedule of successive pulses, determining an amount of therapeutic product delivered over the first schedule of successive pulses, calculating a second schedule of successive pulses required to deliver a next portion of the predetermined bolus dose in dependence on either a difference between an intended delivery quantity for the first portion and an actual delivery quantity delivered over the first schedule, or in dependence on an amount of therapeutic product still to be delivered, and applying the calculated second schedule of successive pulses. The first schedule of successive pulses may be intended to deliver 50% of the specified bolus dose for example. The second schedule of successive pulses may be intended to deliver 50% of the remaining portion of the bolus dose, but it will be appreciated that a different proportion could be used instead. This is an efficient method of increasing the accuracy of delivery of a bolus dose.

Preferably, the control circuitry is further operable to determine an amount of therapeutic product delivered over a previous schedule of successive pulses, calculate a further schedule of successive pulses required to deliver a next portion of the predetermined bolus dose in dependence on either a difference between an intended delivery quantity for the previous portion and an actual delivery quantity delivered over the previous schedule, or in dependence on an amount of therapeutic product still to be delivered, and applying the calculated further schedule of successive pulses. Each schedule of pulses may be intended to deliver 50% of the remaining portion of the bolus dose, but it will be appreciated that a different proportion could be used instead. Still more preferably, the control circuitry is further operable to calculate a final schedule of successive pulses when the amount of therapeutic product remaining to be delivered is less than or equal to a predetermined amount. This prevents the technique from scheduling smaller and smaller groups of pulses; near the end of the delivery of the bolus dose a final schedule is calculated to convey the remainder of the bolus dose—100% of the remainder is delivered by the final schedule rather than the usual 50%.

Preferably, in the bolus delivery mode, the control circuitry is operable to deliver a predetermined amount of therapeutic product by applying a schedule of successive pulses, wherein the control circuitry is responsive to a determination that the predetermined amount of therapeutic product has been delivered before the schedule of successive pulses has been completed to discontinue the delivery of pulses. In this way, over-delivery is inhibited. Preferably, the schedule of successive pulses comprises a first set of pulses followed by a second set of pulses, each pulse in the first set of pulses having a longer duration than each pulse in the second set of pulses. The longer duration pulses deliver more of the therapeutic product. As a result, the delivery slows down towards the end of the schedule of pulses, reducing the risk of over-delivery further when combined with discontinuing the delivery in the event that a required amount of therapeutic product has already been dispensed. It will be appreciated that it would be undesirable to use the shorter pulses for the entire bolus delivery, since this would slow down the rate at which the delivery can be made.

Preferably, the above techniques (delivering 50% and recalculating, discontinuing a schedule of pulses if a target delivery amount has been achieved, and using a shorter pulses towards the end of a schedule of pulses) are used together. For example, the delivery of 50% and recalculating could be used in relation to the overall bolus dose, while the discontinuing of pulses and the variable pulse length could be used within this 50% schedule.

According to another aspect, there is provided a therapeutic product delivery device comprising an actuator according to the above.

According to another aspect, there is provided an actuation method, comprising the steps of:
setting a pulse start time and a pulse duration;
applying an electric current to a semiconductor element in accordance with the set pulse start time and duration to heat a working medium that reversibly expands within a cavity as it undergoes a phase change from a solid to a liquid state, expansion and contraction of the expandable working medium causing a diaphragm disposed adjacent the cavity to deflect, at least one of the pulse start time and pulse duration being set in dependence on a current temperature within the cavity.

In particular, it will be appreciated that while the temperature dependant pulse delivery techniques described herein are preferably used in the context of a semiconductor element which serves both as a heating element and also a temperature sensing element, the basal and bolus delivery techniques are not limited in their application to this, but can also be applied where separate elements are used to heat the working medium and determine the temperature of the working medium. Accordingly, the various pulse scheduling techniques described and claimed herein are envisaged to be used independently of the feature of the two-mode diode (heating and temperature sensing).

Various other aspects and features of the present invention are described in the embodiments which follow.

DETAILED DESCRIPTION

The invention will now be described by way of example with reference to the following Figures in which:
FIG. 1 shows a schematic view of a drug delivery system;
FIG. 2 shows a schematic view of a drug delivery device;
FIG. 3 shows a schematic view of a handset for controlling the drug delivery device of FIG. 2;
FIGS. 4A and 4B schematically illustrate exploded view of an insulin cartridge as a whole and an actuator assembly;
FIG. 5 schematically illustrates a cross section through an insulin cartridge, exposing the layered structure;
FIGS. 6A to 6F schematically illustrate the pumping operation of the insulin cartridge;
FIGS. 7A to 7C schematically illustrates the structure and operation of the one way valves used in the insulin cartridge;
FIG. 8 schematically illustrates a control and power circuit for the diode heating and temperature sending element;
FIG. 9 schematically illustrates the temperature dependence of the operation of the diode in delivering insulin;
FIGS. 10A to 10C schematically illustrate a temperature profile for both basal and bolus mode delivery;

SYSTEM

Figure 1:
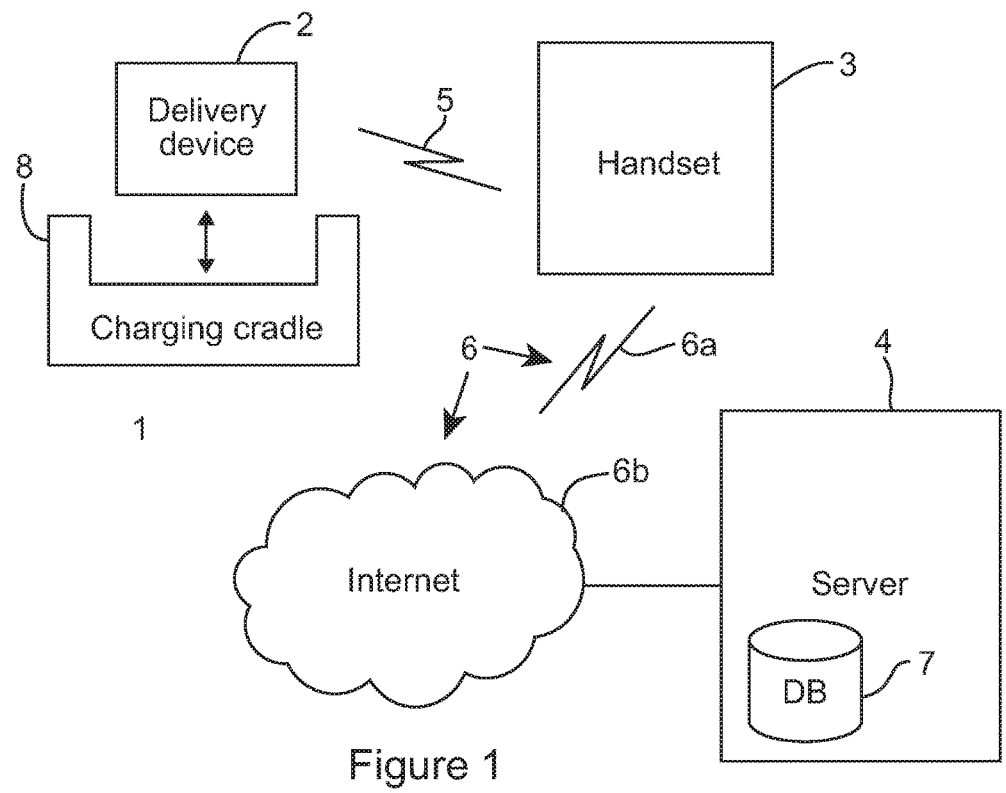

Referring to FIG. 1, a drug delivery system 1 is schematically illustrated. The drug delivery system 1 in this case delivers insulin to a patient. However, it will be appreciated that embodiments of the present invention may be appropriate for delivering drugs other than insulin. The system 1 comprises a delivery device 2 which is worn on the patient's body, a handset 3 (which may appear similar to a smartphone) for controlling the delivery device 2, and a server 4. The delivery device 2 and the handset 3 are able to communicate via a first wireless connection 5, for example a lower power ANT radio connection. The handset 3 and the server 4 are able to communicate via a second wireless connection 6, for example a GPRS mobile data connection 6a and the Internet 6b. The server 4 comprises a patient database 7 for storing patient medical information and other information about the patient. Both the delivery device 2 and the handset 3 are powered by rechargeable batteries. Also shown in FIG. 1 is a charging cradle 8 into which the delivery device 2 is inserted in order to charge the delivery device 2.

Delivery Device

Figure 2:
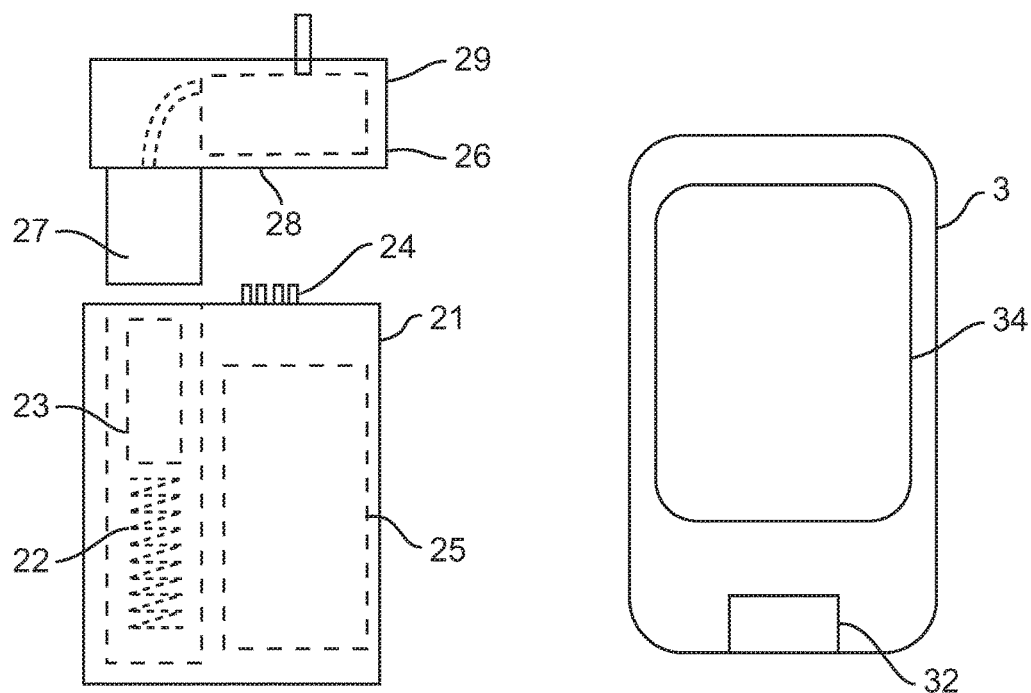
Figure 3:
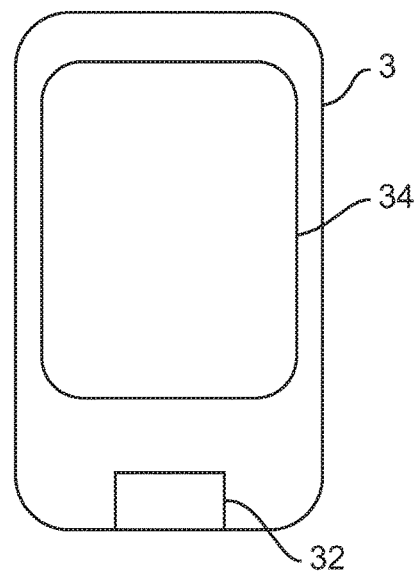

The delivery device comprises two parts, which are detachable from each other, as shown schematically in FIG. 2. The first of the two parts is a body 21, which contains a spring 22, a biasing member 23 including a displacement sensor (for example as described in US2011/0316562), and a set of contact pins 24 for providing an electrical connection with the second part. The body 21 also comprises a battery, control circuitry and a transceiver for communicating with the handset, which are not separately shown in FIG. 2 in the interests of clarity, but are generally represented by element 25. The second of the two parts is a disposable insulin cartridge 26, which comprises a reservoir 27 of insulin, contact pads 28 for providing an electrical connection with the body 21 via the pins 24, a pumping device (a wax actuator, for example as described in GB2443261) for pumping the insulin from the reservoir 27 into the patient's body, and a valve arrangement (for example as described in US2010/0137784). The pumping device and valve arrangement are not separately shown in FIG. 2 in the interests of clarity, but are generally represented by element 29. It will be understood that the body 21 of the delivery device is reusable, while the disposable cartridge 26 is intended to be removed and disposed of when the reservoir 27 has been depleted, or when the cartridge has passed its use by date, or if it develops a fault. A new cartridge can then be engaged with the body 21. While it is preferable that the cartridge is disposable, it will be appreciated that, in principle, the cartridge may be refilled and reused again rather than being disposed of. However, even in this case the cartridge should be removable from the body so that a new (full) cartridge can be used while the original cartridge is being refilled.

In use, the body 21 and the cartridge 26 of the delivery device 2 are physically and electrically connected. The electrical connection is via the pins 24 and pads 28. The physical connection may be provided by clips or any other releasable engagement mechanism (not shown). The control circuitry in the body 21 is responsive to control signals received from the handset 3 via the wireless connection 5 to draw current from the battery and apply an electrical current via the pins 24 and the pads 28 to activate the pumping device within the cartridge 26 to draw fluid from the reservoir 27 through the valve arrangement and out of the delivery device 2 to a patient's body. The rate of delivery of the therapeutic product can be controlled by the control circuitry to achieve a particular basal delivery rate, or bolus dose, by controlling the amount and timing of electrical current to the pumping device. Although the basal rate is set by the handset, once set the delivery device 2 is able to maintain the set basal rate with no further communication from the handset 3. As can be seen in FIG. 2, when the body 21 and the cartridge 26 are in engagement, the reservoir 27 is received within the body 21, displacing the biasing member (and displacement sensor) 23 and compressing the spring 22. The compressed spring applies a biasing force to a base of the reservoir 27 via the biasing member 23. The biasing force does not in isolation force insulin from the reservoir 27 through the valve arrangement and into the patient's body, but when combined with the pumping action of the pumping device, the biasing force pressurises the insulin in the reservoir 27 to refill a pumping chamber in advance of each pumping action. It is the pumping action which drives a controlled amount of insulin from the pumping chamber through an outlet valve and to the patient's body. The reservoir takes the form of a cylinder having a first end from which insulin is drawn under the action of the pump, and a second end opposite to the first end at which the (moveable) base is provided. The base of the reservoir moves inwardly of the reservoir (to effectively decrease the size of the reservoir) as the insulin is pumped from the reservoir, under the biasing force provided by the biasing member 23. The position of the biasing member 23 is dependent on the current fill state of the reservoir—that is, how much insulin is remaining in the reservoir. The position of the biasing member 23, and thus the base of the reservoir 27, is determined by the displacement sensor. The displacement sensor is therefore able to generate a signal indicative of the remaining quantity of insulin in the reservoir. By monitoring the change in the remaining quantity of insulin with respect to time, an actual rate of insulin delivery can be determined. This can be used by the control circuitry to apply corrections to the actual delivery rate by adapting the amount and/or timing of electrical current to the pumping device. The quantity of insulin remaining in the reservoir is transmitted to the handset 3, where it can be displayed to the patient and used as an indicator of when the patient should change the current cartridge for a new cartridge. The control circuitry in the body 21 may also transmit an indication of current battery level to the handset, so that the patient is made aware of when the battery requires recharging.

The delivery device also contains an activity monitor to track exercise (not shown). Exercise can have a significant effect on the amount of insulin needed for good control, so tracking exercise accurately is an important part of effective diabetes management. The activity monitor uses a sensor in the delivery device to detect movement of the delivery device, which can be used to infer when the user is engaged in physical activity. The detected activity is then wirelessly communicated to the handset via the wireless connection 5, where the handset (and the server) is able to track and record the patient's activity. Through an online portal to the server, the patient and permitted medical professionals are able to compare activity peaks with blood glucose to identify how activity is influencing the patient's need for insulin. This can in turn be used to program the handset with appropriate dosages for the patient.

Due to the fact that the patient interfaces with the handset rather than the delivery device itself, the delivery device is able to be made small and discreet, and is provided without buttons or a physical connection to a control unit.

Handset

The handset 3 comprises two transceivers. The first transceiver is for communicating with the delivery device via the first wireless connection 5, while the second transceiver is for communicating with the server 4 via the second wireless connection 6. The handset also comprises a processor for running control software. The control software monitors the patient's condition and reports it to the central server 4, and controls the delivery of insulin doses to the patient by transmitting control signals to the delivery device 2. The handset 3 also comprises a touch screen display 34, which displays information to the user and provides a user interface for the user to input data, modify the basal rate, and trigger extraordinary bolas doses.

As well as wirelessly controlling the pump, the handset 3 also has an integral blood glucose meter 32. The blood glucose meter 32 detects the amount of glucose in the patient's blood. The blood may be analysed at the meter 32 by pricking the patient's finger and depositing a droplet of blood on a slide, which is inserted into the meter 32. The detected blood glucose level can be brought to the attention of the patient on the handset 3, and the patient can decide to trigger a bolas dose based on the blood glucose information. The result of every blood glucose test is automatically logged by the software and becomes immediately available for reference via the server 4 to the patient, medical professionals and even family members (such as parents). More generally, the handset 3 runs various software applications which help the user (and other authorised parties) to keep track of diet, insulin, blood glucose and exercise (which as explained above is recorded automatically from a sensor in the delivery device). By automating data collection, the handset 3 eliminates, or at least reduces, the need for a diabetes journal and ensures that comprehensive and accurate clinical information are constantly available to the patient and medical professionals via the server 4.

When controlling the delivery device, the handset 3 sends wireless signals to the delivery device 2 to deliver regular periodic doses of insulin at a pre-determined basal rate, which is set on the handset 3 according to the recommendations of a medical professional. The basal rate may be adjustable by the user within certain constraints. However, the software is configured such that it is not allowed for the basal rate to be adjusted remotely by third parties such as doctors. The hand-held device 3 also allows the user to trigger extraordinary bolus doses, for example after eating carbohydrates or performing exercise. As with a basal dose, the bolus dose is delivered by the delivery device 2 in response to control signals sent wirelessly from the handset 3. The user is able to input the volume of carbohydrates which have been consumed at a relevant time and is also able to input periods of exercise and the hand-held device is able to recommend adjustments to the basal rate or when a bolus is needed. As discussed above, the glucose monitor 32 may have an influence on the dosage. All of this information is transmitted to the server 4. The hand-held device 3 also receives information from the delivery device 2, for example to indicate whether it is faulty or when the insulin cartridge needs to be replaced. It also provides an indication of battery level.

Server

It will be understood from the above that the handset 3 and the delivery device 2 monitor and record clinical information while delivering insulin according to the body's needs. By providing this information to the server 4, it can be made almost immediately available to all those who need to see it. In particular, a mobile connection to a secure online management portal makes it possible for patients, clinicians and parents to be made constantly aware of, and able to react to, changing conditions. A diabetes clinic with patients using the system is able to see the current status of all its patients on a single screen, delivered to the clinic in real time. The portal can be accessed over the Internet in the clinic or through a smartphone. In addition to making it possible for a patient to access their latest clinical information online, it is possible for the patient to see simple visual analysis of their data, for example to identify trends and patterns in their blood sugar, and to immediately see their insulin dosing habits. This information can all be viewed using a simple online web portal that can be accessed from home, from work or from a smartphone. The server can also transmit SMS messages to a child's parents to let them know their child's information and state of health.

A patient using the system is provided with a personal login to the secure mobile diabetes management portal. Once logged in the patient can see all of their automatically collected data in the form of charts and graphs to help them understand where they might need to make adjustments. Exercise habits are mapped out in pie charts. An indication of exactly how and when the patient's insulin was delivered is provided. The patient's clinicians are able to see the same analysis and information, enabling them to call or text the patient whenever needed with guidance and advice.

From a single online dashboard screen, the clinic has access to the status of all the patients on the system; including current blood sugar, average blood sugar, insulin dosing, hypo frequency and blood testing habits. At a glance, anyone having difficulties can easily be identified for an immediate response. With a single click, all the data for a patient is analysed and charted to identify trends, patterns and problems. Using the portal, clinics can completely reorganise the way in which patients are managed. Text and email can be used to check on recent events. Clinic visits are focused completely on current and accurate information.

Cartridge Structure

Figure 4A:
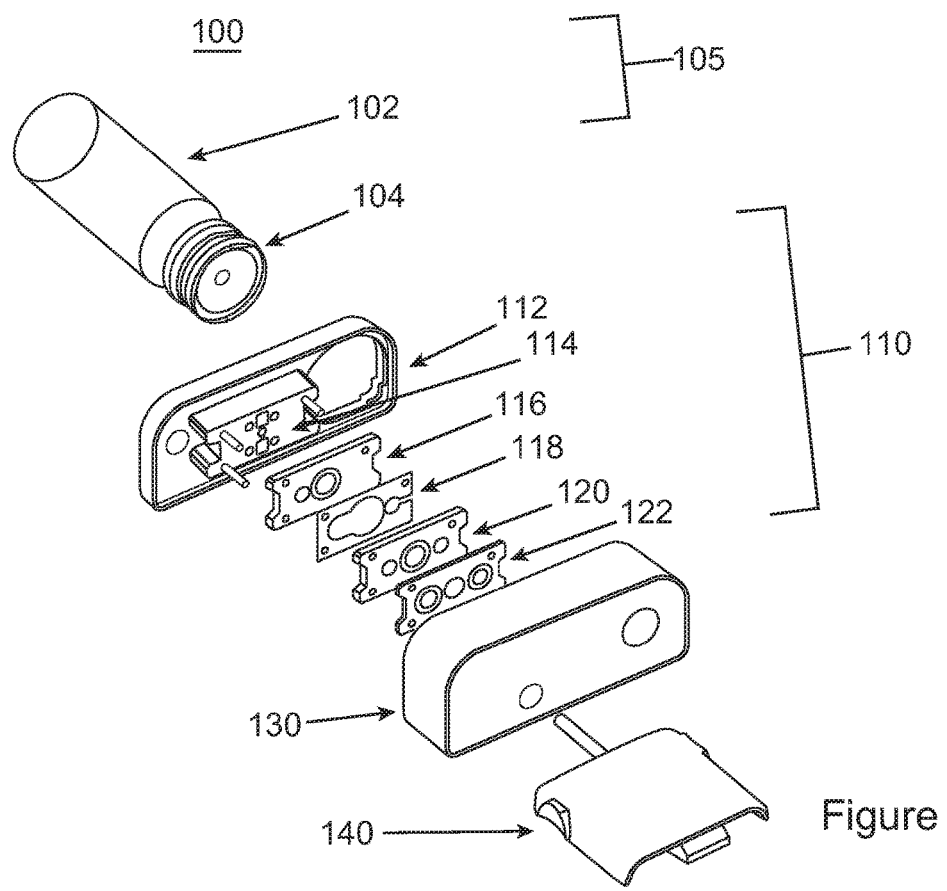

Referring to FIG. 4A, a schematic exploded view of the structure of a disposable cartridge 100 is provided. From top left, the cartridge 100 comprises a reservoir assembly 105. The reservoir assembly 105 comprises a reservoir 102 and a plunger assembly 104. The cartridge 100 also comprises a pump stack 110. The pump stack comprises an actuator assembly 112, a piston 114, a gearing/seal membrane 116, an occlusion layer 118, a fluidic layer 120 and a fluidic membrane 122. The cartridge 100 further comprises a housing assembly 130 and an infusion set 140.

Figure 4B:
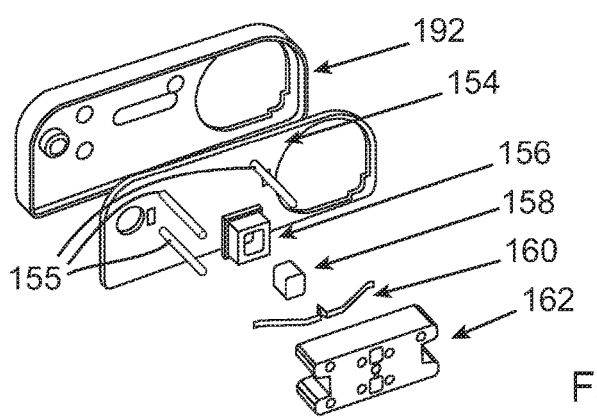

Referring to FIG. 4B, a schematic exploded view of the structure of the actuator assembly 112 is provided. From top left, the actuator assembly 112 comprises a base 152, a PCB (circuit) layer 154 from one side of which protrudes three conductive pins 155, an actuator insert 156, a block of wax 158, a diode assembly 160, and an actuator body 162.

In use, the reservoir 102 stores the insulin (or other therapeutic product) which is to be delivered to the patient's body, and the plunger assembly 104 is urged inwardly of the reservoir 102 by a biasing member on the main body of the delivery device, onto which the cartridge 100 is fitted. It will be understood that the reservoir 102 is generally cylindrical in shape, and the plunger 104 forms a moveable base end of the cylinder. The other end of the cylinder is formed by an internal structure of the housing assembly 130. The pressure applied by the plunger 104 on the insulin in the reservoir 102 pressurises the therapeutic product in the reservoir 102. When assembled, the reservoir 102 is received through an aperture in the base 152 of the actuator assembly 112 to engage with the housing assembly 130, which provides a channel for carrying the therapeutic product from the reservoir 102 under the pressure exerted by the plunger 104 through the fluidic membrane 122 and into a pumping chamber within the fluidic layer 120. From the pumping chamber, the insulin can be pumped in a controlled manner (under the influence of the piston 114) out to the infusion set 140, again via a channel in the housing assembly 130. The housing assembly 130 also has a channel for carrying insulin to the occlusion layer 118 when there is a blockage preventing the insulin exiting via the infusion set 140. The fluidic layer 120, fluidic membrane 122 and part of the housing assembly 130 form a valve arrangement. This valve arrangement comprises the pumping chamber, an inlet valve through which insulin passes from the reservoir 102 to fill the pumping chamber, an outlet valve through which insulin passes when the pumping chamber is compressed by the piston 114 causing the insulin to be expelled from the pumping chamber and out through the outlet valve, and a breakthrough valve through which the insulin is forced in the event of a blockage between the outlet valve and the delivery site on the patient. The fluidic membrane 122 comprises silicone membranes which are stretched over mesa structures in the fluidic layer 120, forming one-way valves by way of the mechanism described in US2010/0137784 (for example). The gearing membrane 116 is disposed between the piston 114 and the pumping chamber in the fluidic layer 120. The gearing membrane 116 both seals the pumping chamber and is displaced by the piston 114 on actuation to push liquid out of the pumping chamber and towards the outlet valve.

In FIG. 4B, the base 152 comprises an aperture through which the reservoir 102 is received to engage with the housing assembly 140, and a smaller slot aperture which exposes contact pads (not shown) on the PCB assembly 154 to the outside of the cartridge 100. Pins on the device body of the delivery device can therefore access the contact pads to provide an electrical connection between the two parts of the delivery device. The base 152 also comprises lugs (not shown) which are able to be inserted into the device body to engage with clips inside the device body to hold the two parts of the delivery device together. On the other side of the PCB assembly 154 are the conductive pins 155. These extend away from the PCB assembly (circuit layer) 154 through the various layers of the cartridge 100 described above. The conductive pins in the present embodiment extend to engage with the housing assembly 140, and therefore pass through all interior layers of the cartridge 100. These conductive pins effectively serve three purposes. Firstly, they properly align the layers of the cartridge 100 at the point of assembly, and ensure that they do not come out of alignment when the cartridge is in use. Secondly, they provide a conductive route between the PCB assembly 154 and the occlusion layer 118, these layers otherwise being sealed away from each other by the gearing membrane 116. In the case of a blockage, as explained above the insulin exiting the outlet valve is routed to the occlusion layer 118 via a breakthrough valve. In particular, the insulin is routed to a detection region comprising two contact points, each contact point being electrically connected to one of the conductive pins 155 (the third conductive pin being for structural purposes only). The presence of insulin at the detection region bridges the gap between the two contact points, thereby completing a circuit via the conductive pins to the PCB assembly 154, resulting in detection of the blockage at the PCB assembly 154 (or at control circuitry within the device body, which is electrically connected to the PCB assembly 154 via the contact pads), which may result in the sounding of an alarm on one or both of the delivery device and the handset. Thirdly, in the case of a leak permitting insulin to breach its designated channels through the various layers between the gearing membrane 116 and the housing assembly 130, the leaked insulin may spread out to electrically connect together the conductive pins (directly, at any one or more layers), thereby triggering an alarm as if a blockage had been detected.

The actuator assembly 112 also comprises an actuator insert 156 which is mounted to the PCB assembly 154 and receives a block of wax 158. A diode assembly 160 is provided, which includes a diode which will be embedded within the wax 158, and a conductive element for connecting the diode to the PCB assembly 154. The actuator insert 156, the wax 158 and the diode assembly 160 are trapped on assembly by the actuator body 162, which is received on the conductive pins 155, and which is able to receive the piston 114 as shown in FIG. 4A.

Figure 5:
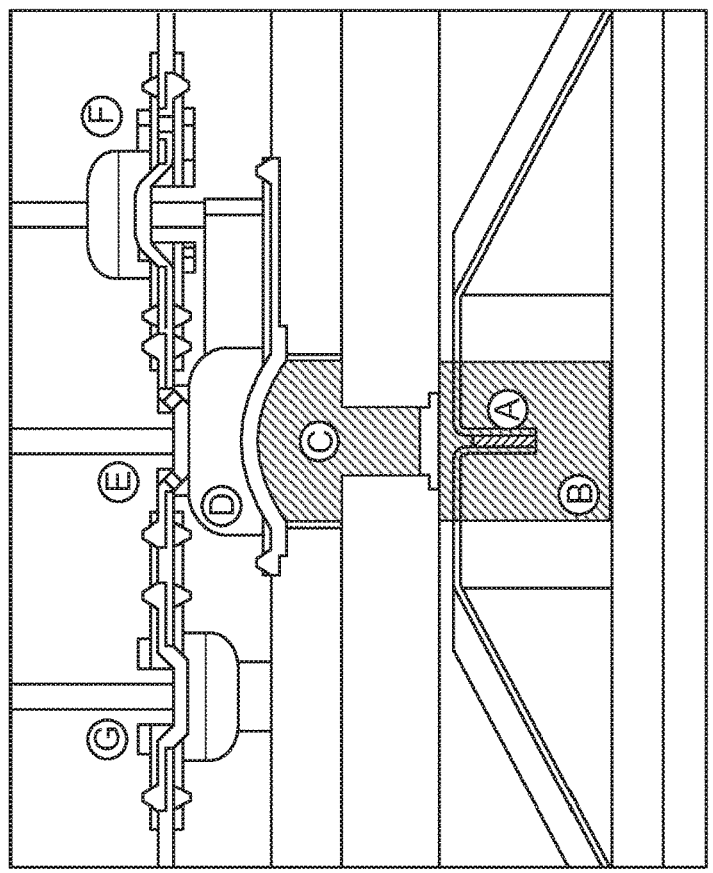
Figure 5:
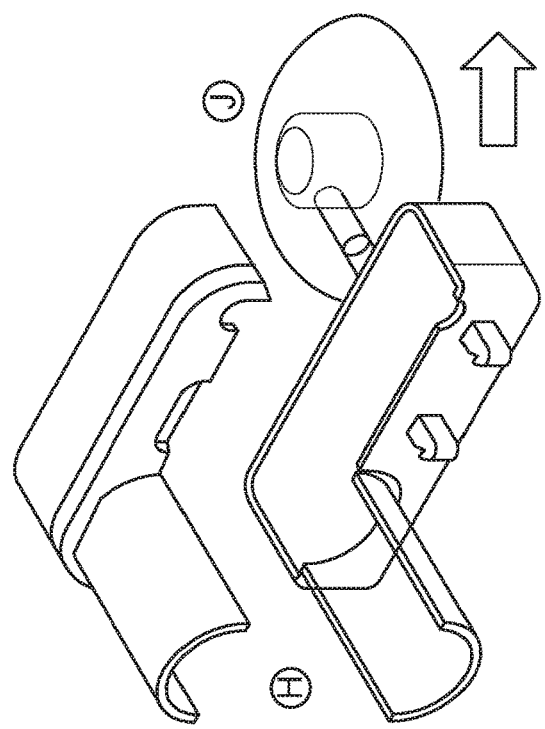

FIG. 5 schematically illustrates a cross section through the cartridge 100. In the cross section, a diode A is shown embedded within wax B. The wax B is sealed into the actuator insert by the actuator body, which sits above it, and which comprises a diaphragm which seals in the wax, but which is resiliently deformable to deflect upwards when the wax expands, and to return to its original position when the wax contracts. A piston C extends from proximate the wax B (the piston C being separated from the wax B by the diaphragm as a first flexible membrane) to a second flexible membrane which separates the piston from a pumping chamber D. The pumping chamber D is fed insulin by a reservoir H via an inlet valve E. An outlet valve F is arranged to allow insulin from the pumping chamber to exit under the pumping action of the piston C. An occlusion (breakthrough) valve G is provided which, as discussed previously, allows insulin to pass through it when there is a blockage between the outlet valve F and the infusion site on the patient, for example within infusion set J. It will be appreciated that the valves E, F and G are formed by the sandwiching of the components 120, 122 and 130 of FIG. 4A.

Figure 6D:
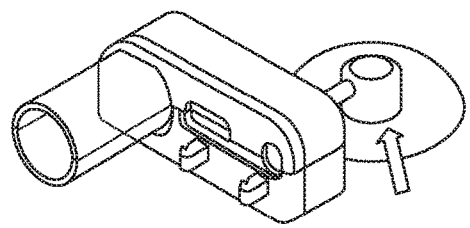
Figure 6D:
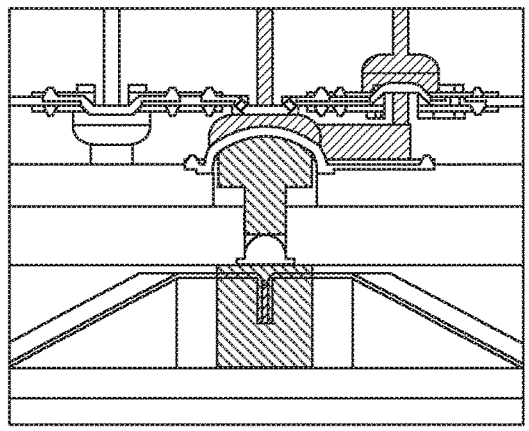

FIGS. 6A to 6F schematically illustrate the operation of the cartridge of FIG. 5. In FIG. 6A, a syringe and needle is used to pierce a septa in the base of the cartridge and fill the cartridge. Initially, the insulin fills the reservoir H. Referring to FIG. 6B, once the reservoir is full, the liquid progresses through the pumping chamber D. The liquid continues through the valves to prime the infusion set J. To start pumping the insulin, an electric current is applied, as shown in FIG. 6C. This causes the diode A to heat up, melting the wax B, which causes the wax B to expand. In FIG. 6D, it can be seen that the wax expansion pushes the piston C into the pumping chamber D, reducing the capacity of the pumping chamber D and causing the insulin in the pumping chamber D to be displaced towards the outlet valve F (it will be appreciated that the insulin cannot exit the pumping chamber D through the inlet valve E, since the valve only permits the passage of fluid in one direction—into the pumping chamber). The liquid is therefore forced through the one-way outlet valve F to the infusion site via the infusion set J.

Figure 6E:
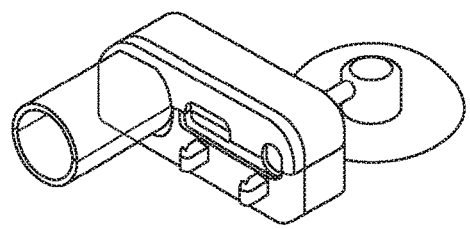
Figure 6E:
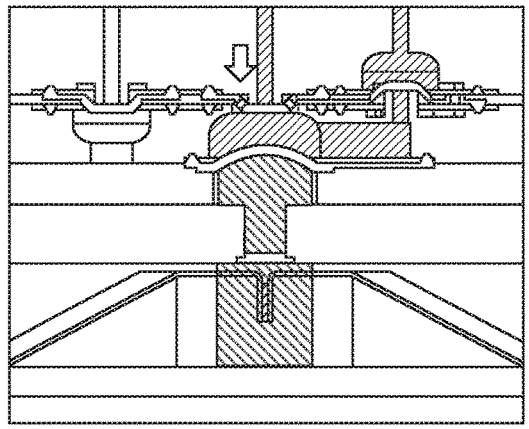
Figure 6F:
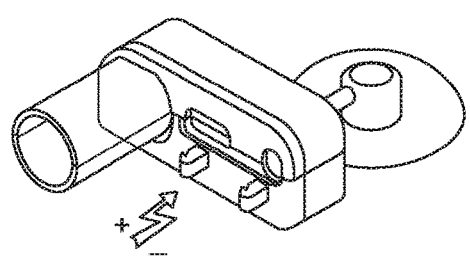
Figure 6F:
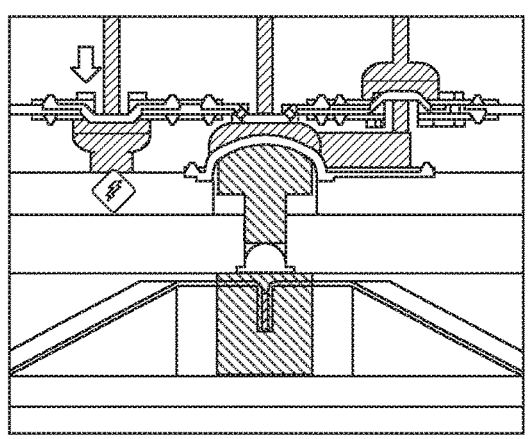

In FIG. 6E, the electric current has been discontinued, allowing the diode and the wax to cool and contract, consequently permitting the piston C to move back out of the pumping chamber D to its original position. It will be appreciated that one or more of the membrane (diaphragm) between the wax and the piston, the membrane between the piston and the pumping chamber, and the pressure applied by the fluid in the reservoir through the inlet valve E and into the pumping chamber, may provide a bias to the piston C to keep it in its original position except for when the expansion of the wax B overcomes the bias. When the piston C returns to its original position, the pumping chamber D refills with liquid through the one-way inlet valve. This completes the pumping cycle. FIG. 6F demonstrates what happens if there is an occlusion during the pumping action. In FIG. 6F, as with FIG. 6C, an electric current is applied to the diode to heat the wax B and move the piston C into the pumping chamber D. The fluid from the pumping chamber D is forced through the outlet valve F, as with FIG. 6D, but in this case there is a blockage preventing the fluid from reaching the infusion site. This causes a build-up in pressure to the one way breakthrough (occlusion) valve G sufficient for the fluid to be redirected through the occlusion valve G to be conveyed to a detection region (on the occlusion layer 118 as discussed above).

Referring to FIGS. 7A to 7C, the structure and operation of the one-way valves used for each of the inlet valve, the outlet valve and the occlusion valve are schematically illustrated. In FIG. 7A, liquid is under pressure at the inlet of the valve in a first direction (the direction of the arrow). The pressure of the liquid in FIG. 7A is insufficient to open the valve and allow the liquid to pass through. In FIG. 7B, the pressure is increased, and is now sufficient to deflect a membrane away from the mouth of the inlet, allowing the liquid to enter into a chamber. The membrane comprises apertures which then allow the liquid in the chamber to exit the valve. It is this mechanism which allows liquid to pass through the valve in a first direction (following the direction of the arrows through the valve as shown in FIG. 7B), subject to pressure at the inlet being sufficient. In the case of the three valves in the cartridge 100, the pressure required may be the same or different for each of these. Referring now to FIG. 7C, liquid is under pressure at the outlet to the valve (attempting to flow in the direction of the arrow). While this liquid can enter the chamber through the apertures in the membrane, it is unable to pass through the portion of the membrane which is seated on the inlet, and therefore the liquid cannot pass through the valve in this direction. This valve mechanism is described in detail in US2010/0137784.

Wax Actuator and Pulse-based Delivery Control in Basal and Bolus Modes

As described above, the wax actuator that delivers the pump stroke is heated by a diode in the wax. The amount of insulin dispensed by way of this mechanism varies according to the starting temperature of the wax prior to the application of a pulse of electric current across the diode. In order that the diode can be pulsed to deliver an exact amount of insulin, the temperature needs to be determine accurately. In the present case this is achieved using the same diode (as for heating the wax) to measure the temperature in exactly the right place.

Referring to FIG. 8, circuitry for controlling the actuator is schematically illustrated. The control circuitry comprises a microcontroller (MCU) 810 for controlling the application of an electric current to a diode 820 to control the amount and timing of the delivery of the therapeutic product. The diode 820 can be used in two modes. In a first mode, a constant high current source 840 (of for example around 1.3 A) is applied to one terminal of the diode 820 (the other terminal of the diode 820 being connected to ground 830) under the control of the microcontroller 810. This causes the diode 820 to generate heat, which melts the wax and drives the actuator. This pulse of current will be applied for a precisely controlled amount of time. In a second mode, a constant low current source 850 (of for example around 100 μA) is applied to one terminal of the diode 820. A measuring device 860 is connected across the diode 820, and is able to measure the voltage drop across the diode. It will be appreciated that the resistance of a diode is a function of its temperature. Given that the constant low current source is (a) constant, and (b) known, it is possible to derive the resistance of the diode from the known current and the measured temperature. The relationship between the resistance of the particular diode and its temperature is known in advance, making it possible to derive the temperature of the diode at the time of measurement. The microcontroller 810 derives the temperature from the measurement taken by the measuring device 860 and uses the derived temperature when driving the diode in its first mode, in the application of pulses for both basal and bolus delivery.

Figure 9:
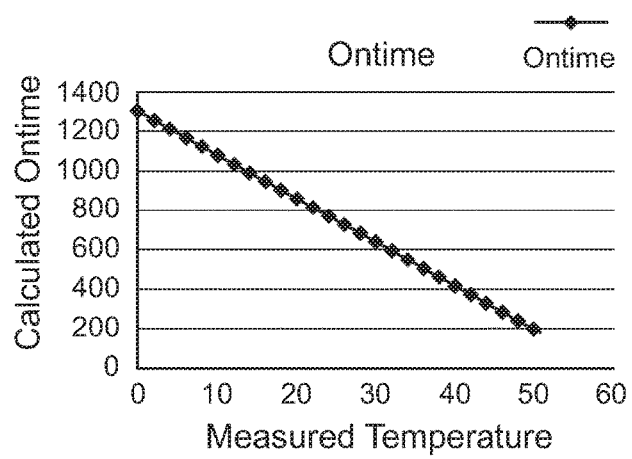

Referring to FIG. 9, at the top left expressions are given for the required on time (as a function of temperature) for a pulse in a basal mode delivery of 0.05 units (0.5 μl of insulin), and for a pulse in a bolus mode delivery of 0.1 units (1 μl) of insulin. These are as follows:

On time (basal) in ms=1300−(measured temperature (in ° C.)*22)

On time (bolus) in ms=1800−(measured temperature (in ° C.)*22)

It will be understood that this will result in a longer pulse duration to achieve the higher per-pulse delivery amount of 0.1 U (usual bolus pulse) compared with 0.05 U (usual basal pulse).

The table on the left of FIG. 9 shows the required on time (basal mode delivery) for a range of temperatures from 6° C. up to 50° C. It can be seen that the required pulse duration to achieve a given delivery of insulin is much shorter when the starting temperature of the wax is high, than at low starting temperatures. The graph at the bottom right of FIG. 9 illustrates this graphically.

It will be appreciated that without knowing the starting temperature of the diode and wax, it would not be possible to accurately control the amount of insulin being delivered by way of a single pulse. The use of the diode in a second mode to determine the temperature of the wax immediately surrounding the diode makes it possible to achieve the required accuracy. At the measurement device, the determination of pulse duration based on temperature can be conducted either by way of a calculation, or by referring to a look up table (or two look up tables—one each for basal and bolus/basal delivery) storing a correspondence between starting temperature and pulse duration.

Figure 10A:
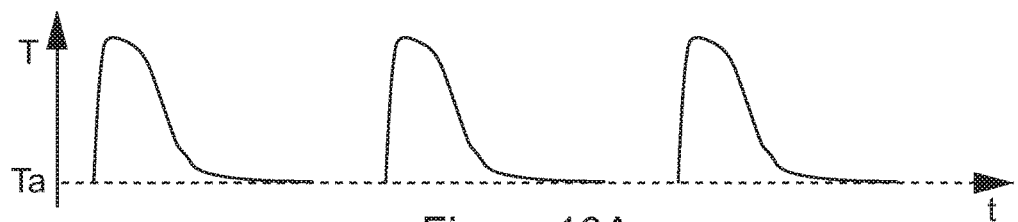
Figure 10B:
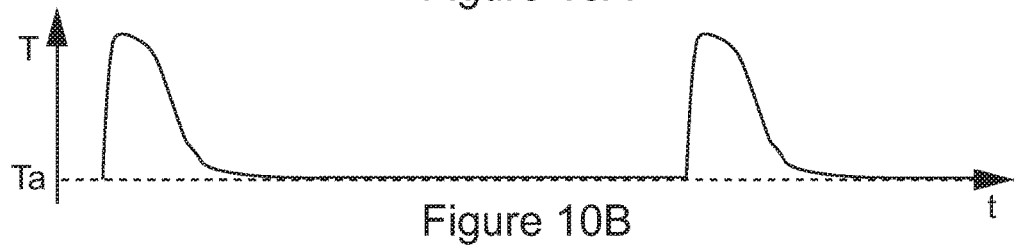

Referring to FIGS. 10A, 10B and 10O, a pulse-based method for controlling the delivery of insulin is illustrated for both basal and bolus delivery. Typical basal delivery rates may range from 0.05 units (0.5 μl) of insulin per hour to 2 units (20 μl) of insulin per hour, or even to 5 units (50 μl) of insulin per hour in exceptional cases. Bolus doses (one off doses, in response to e.g. food consumption) may vary widely, but may be up to 30 units (300 μl), or possibly more. Each of FIGS. 10A to 10O is a graph showing temperature, T (vertical axis) against time, t (horizontal axis). FIG. 10A relates to basal delivery. In basal delivery mode, pulses of electric current are delivered to the diode on a regular basis, each pulse being separated from the next pulse usually by at least 30 seconds, and more usually the order of a few minutes. Each pulse is intended to deliver a fixed amount of insulin, and may be of order of one Joule of energy. The length of each pulse is calculated based on the starting temperature just before the pulse is started, as described above in relation to FIG. 9. As can be seen from FIG. 10A, each pulse causes the temperature of the working medium to rapidly increase while the diode is being supplied with a high current, and then to decay back to an ambient temperature $T_a$ when the pulse ends and current no longer flows through the diode. In general, it can be expected that each new pulse will start from the ambient temperature $T_a$, due to the time delay between each pulse, but in any case any changes in the ambient temperature will be compensated for by changing the pulse duration. Each pulse delivers a predetermined amount of insulin, which may for example be 0.05 units (U), or 0.5 µl of insulin. In order to change the basal rate dosage, the frequency with which the pulses are applied to the diode is modified. For example, it can be seen that FIG. 10B, which also relates to basal mode operation, is being pulsed at half the frequency (double the interval between pulses) as is the case in FIG. 10A. This will result in a delivery rate which is half that of FIG. 10A.

Figure 10C:
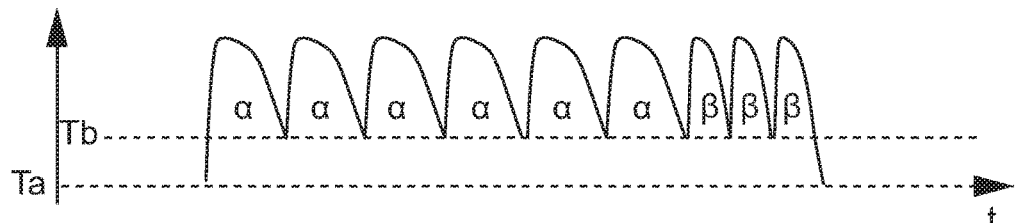

FIG. 10C on the other hand relates to a bolus delivery. In this case, it is desirable to deliver the desired dose of insulin as quickly as possible. In order to achieve this, each new pulse is started as soon as the temperature at the diode drops below a predetermined threshold $T_b$. This threshold temperature $T_b$ is set preferably at, or at least near, a value at which the wax will have solidified, the diaphragm sealing the wax chamber will have reverted to its original position, the piston will have retracted to its original position and the pumping chamber will have been refilled from the reservoir. At this point, the pumping system can be considered to be reset, and a new pumping cycle can be restarted. For FIG. 10C it can be seen that the first pulse is required to start at the ambient temperature $T_a$, while the subsequent pulses all start at the predetermined temperature $T_b$. As a result, the subsequent pulses can be shortened relative to the first pulse (based on the equations discussed in relation to FIG. 9), because only the first pulse needs to start from the ambient temperature $T_a$. It will also be noted from FIG. 10C that there are two pulse types, denoted as α and β respectively. The α pulses each deliver 0.1 units of insulin, whereas the β pulses each (like the basal pulses) deliver 0.05 units of insulin. It will be appreciated that none of FIG. 10A to 10C are to scale, and particularly the pulses of FIG. 10C are not to scale relative to the pulses of FIGS. 10A and 10B. In bolus delivery two types (durations) of pulse are used so that in an early stage of bolus delivery the insulin can be delivered as quickly as possible (the α pulses delivering more insulin per pulse than basal pulses), while in the later stage of bolus delivery the risk of over-delivery can be reduced by slowing down the delivery rate, and the smaller dose per pulse enables the overall dose to be controlled with more accuracy (to the nearest 0.05 units rather than to the nearest 0.1 units).

Figure 11:
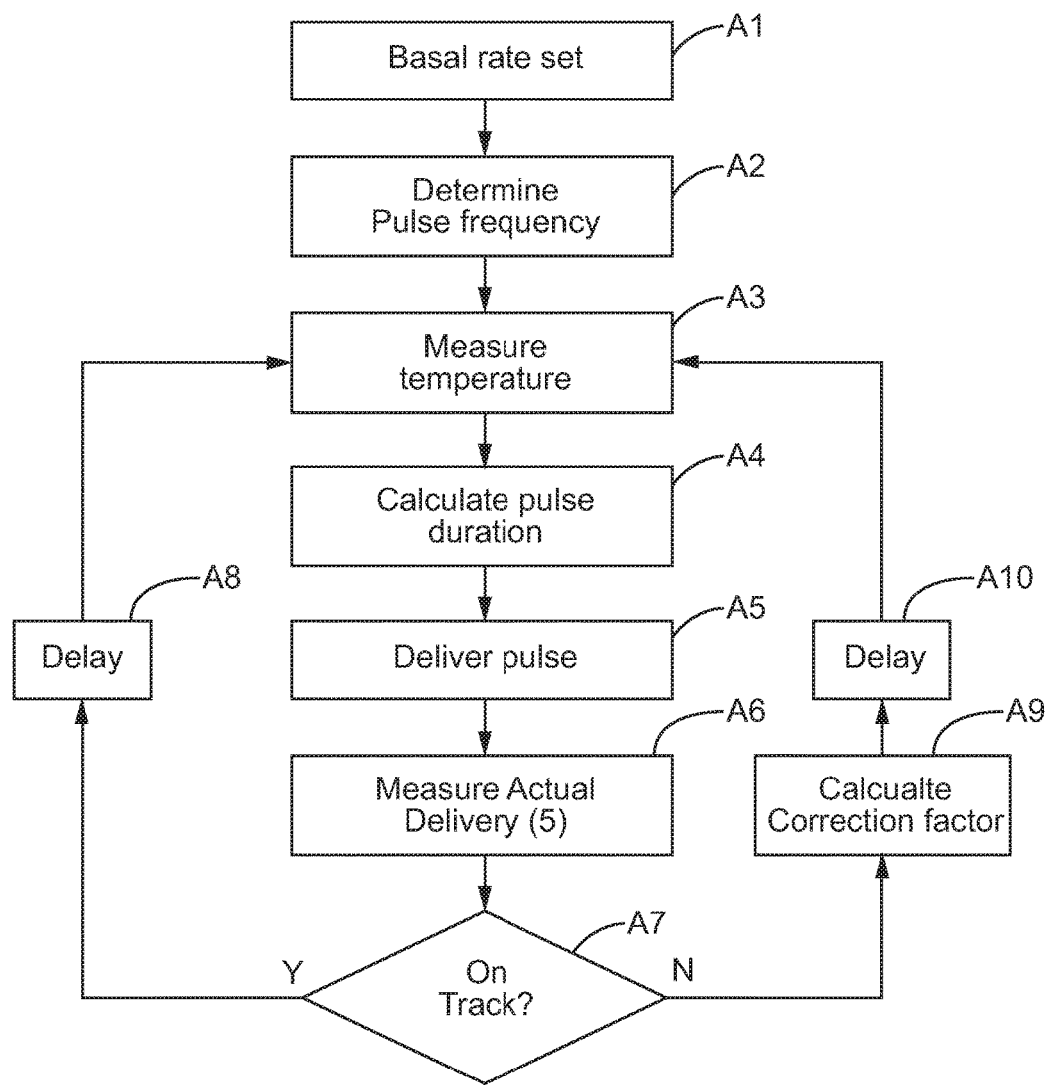
FIG. 11 is a schematic flow diagram for basal delivery.

Referring to FIG. 11, a schematic flow diagram illustrating a basal delivery process is provided. At a step A1 a basal delivery rate is set, preferably at the handset and communicated to the delivery device. At a step A2, the delivery device determines a pulse frequency (pulses per hour) required in order to achieve the desire basal rate. At a step A3, just before a pulse is to be delivered (at a time derived from the pulse frequency determined at the step A2), the temperature of the diode is determined, and is used to calculate a pulse duration at a step A4. Then, at a step A5, the pulse is delivered to the diode in the form of the application of a constant current. As discussed above, this heats up the wax, deflects the diaphragm and drives the piston into the pumping chamber, expelling insulin from the pumping chamber out through the outlet valve. When the pulse duration has expired, the constant current is cut off, the diode cools, the wax cools, the diaphragm moves back to its original position, the piston resets, and the pumping chamber refills. At a step A6, the actual delivery rate (the amount of insulin actually delivered) over the last 5 (or more generally, n) pulses is determined, based on the amount of movement of the displacement sensor which tracks the position of the plunger in the reservoir. At a step A7 it is determined whether delivery is on track; that is, whether the actual delivery is the same or substantially the same as the amount of insulin intended to be delivered over the course of the last 5 pulses. If yes, then following a delay A8 which depends on the pulse frequency set at the step A2, the process returns to the step A3 where the temperature is again calculated in preparation for the next pulse, and the subsequent steps are repeated. If at the step A7 it is determined that the actual delivery amount is higher or lower than the intended delivery amount, then at a step A9 a correction factor for the next pulse is calculated. In the case that the actual delivery amount over the previous 5 pulses was higher than the intended delivery amount, then the correction factor will result in a shorter next pulse to compensate by delivering a smaller amount of insulin. In the case that the actual delivery amount over the previous 5 pulses was lower than the intended delivery amount, then the correction factor will result in a longer next pulse to compensate by delivering a larger amount of insulin. The correction factor is preferably applied only for the following pulse, but in some cases it may be necessary or desirable to correct the next m pulses, or to make a permanent or semi-permanent correction to correct for a systematic error in delivery. Then, following a delay A10 which depends on the pulse frequency set at the step A2, the process returns to the step A3 where the temperature is again calculated and a new pulse delivered at the step A5 based on a temperature-dependent calculation at the step A4 which in this case includes the correction factor obtained at the step A9. The step A6 is then repeated, again based on the previous 5 pulses (the 5 pulse "window" moves to track the current pulse). By following this process, the actual delivery of a basal dose is able to continuously correct itself.

Figure 12:
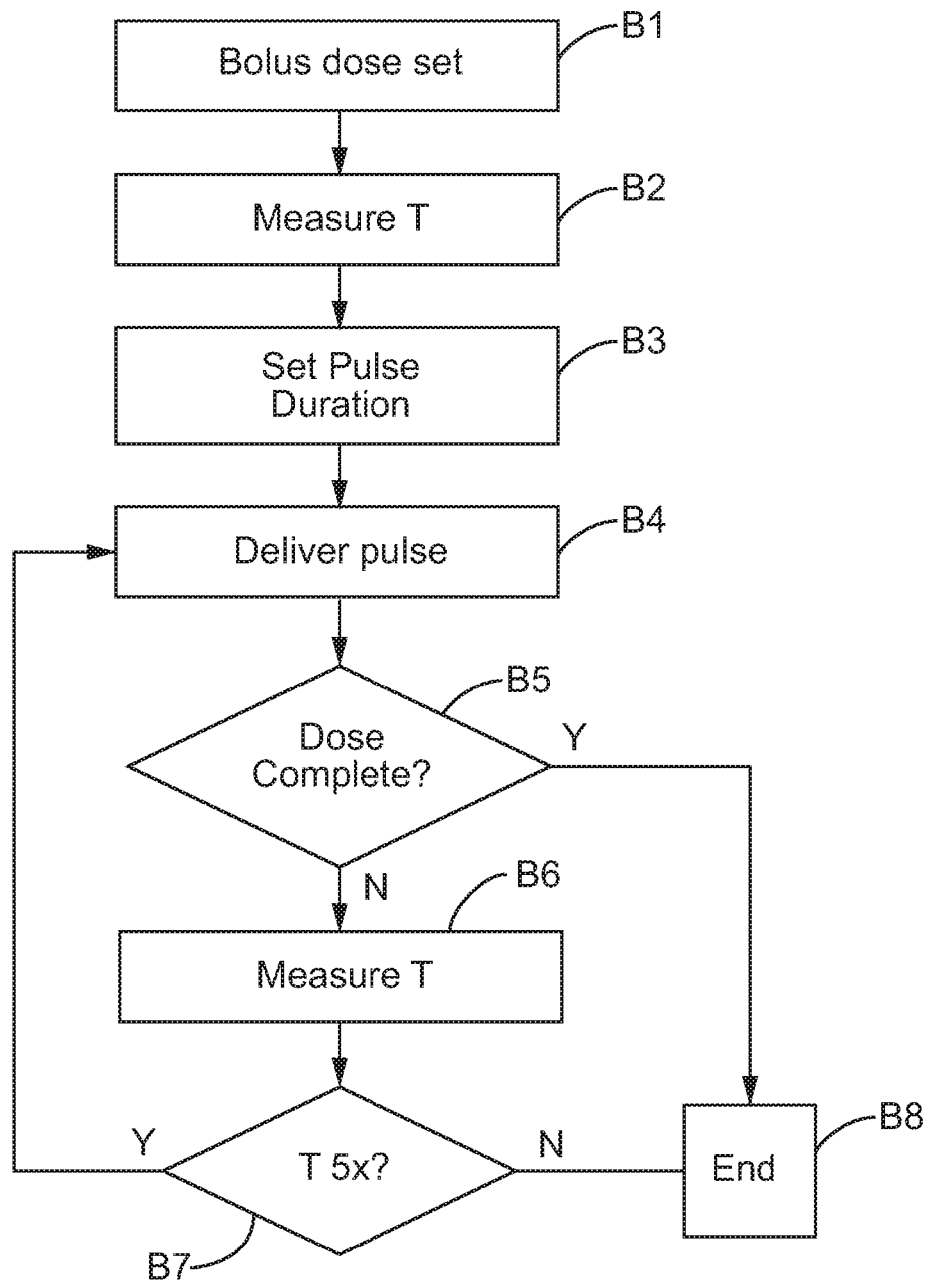
FIG. 12 is a schematic flow diagram for bolus delivery.

Referring to FIG. 12, a schematic flow diagram illustrating a bolus delivery process is provided. At a step B1, a bolus dose is set. Preferably this dose is set at, and transmitted to the delivery device from, the handset. The patient may trigger a bolus dose based on a type and amount of food which they have consumed. A bolus delivery starts immediately. At a step B2, the ambient temperature at the diode is measured, and is used to set a first pulse duration at a step B3. The first pulse is then delivered at a step B4. Then, at a step B5 it is determined whether the complete bolus dose has been delivered. If it has, then the process ends at a step B8. If not, then at a step B6 the temperature is continuously monitored (loop with a step B7), until it is determined at the step B7 that the temperature has dropped to or below the predetermined threshold temperature (x) referred to above. At this point, delivery of the next pulse is triggered by returning to the step B4. The duration of each of the subsequent pulses (that is, each pulse after the first) is fixed, since the predetermined threshold temperature is the starting temperature for each pulse (except the first), and is known in advance.

Figure 13:
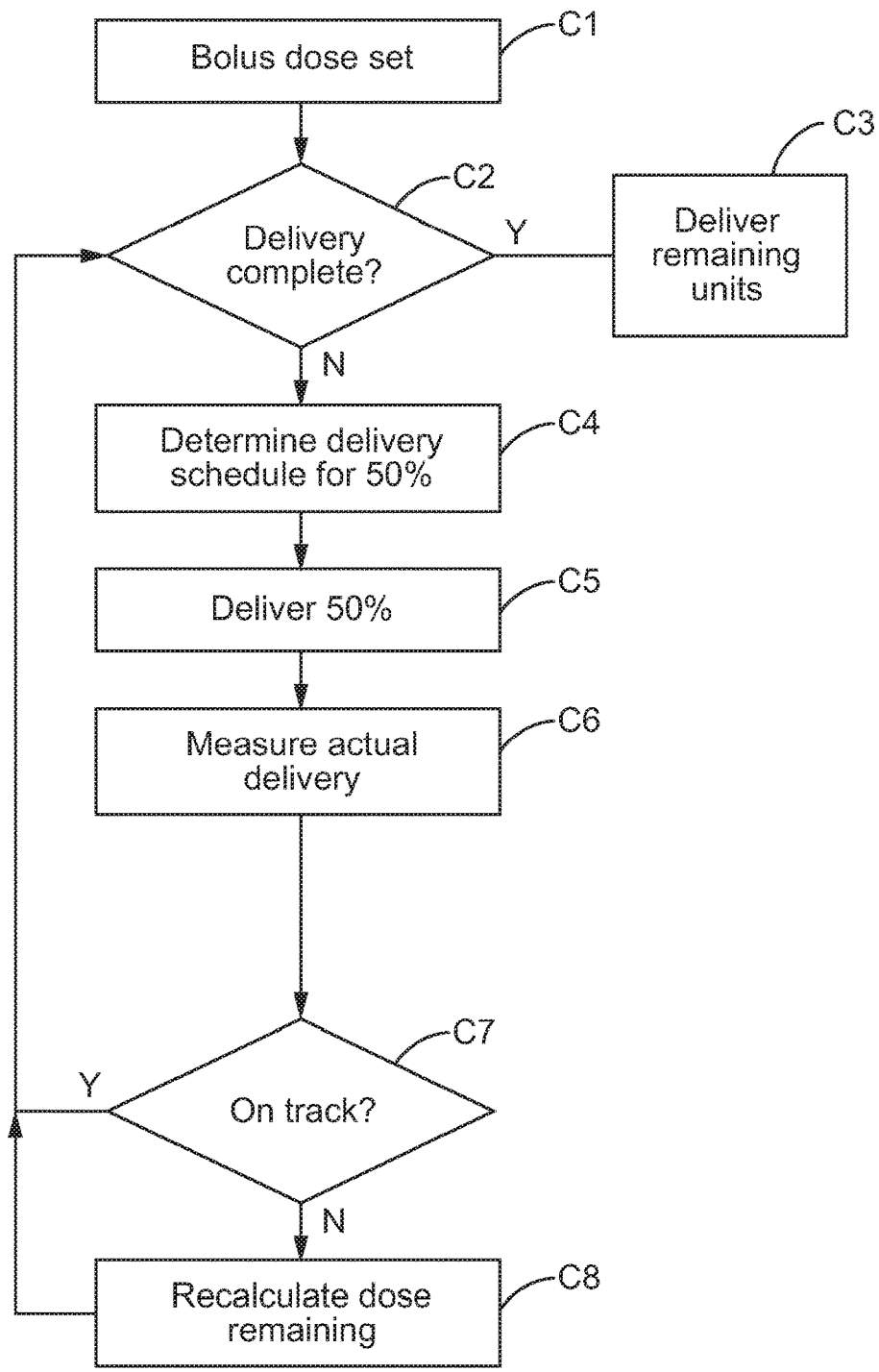
FIG. 13 is a schematic flow diagram for a first correction technique for bolus delivery.

Referring to FIG. 13, a schematic flow diagram is provided which illustrates a first technique for correcting for over-delivery or under-delivery of a bolus dose. At a step C1, a bolus dose is set. At a step C2, it is then determined whether there are less than a predetermined number of units of insulin to be delivered (for example 0.5 units). If so, that insulin is simply delivered (potentially using the technique described below in relation to FIG. 14). If there are more units than this (still) to be delivered, then at a step C3 a delivery schedule for the first 50% of the bolus dose is determined. The determined 50% is then delivered at a step C4, and then at a step C5 an actual amount of delivery over the course of the first 50% is measured using the displacement sensor. At a step C6 a comparison between the intended and actual delivery is made. If the comparison reveals that the delivery is on track, in that the actual amount of insulin delivered by the bolus pulses is substantially 50% of the bolus dose, then the process returns to the step C2, leading either to delivery of the remaining dose in one go (at the step C3) or the determination of a delivery schedule for 50% of the remainder. This process continues until the condition in the step C2 is met and delivery completes at the step C3. If at the step C6 it is determined that the delivery is not on track, in that either more or less insulin has been delivered than was planned, then at a step C7 a recalculation of the dose remaining takes place before the process reverts to the step C2, where the recalculated dose remaining is used as the basis for determining a schedule of pulses required to deliver the remaining insulin of the bolus dose. This has been found to offer a good compromise between accuracy and speed. If continuous correction were to take place in this way then this would be computationally expensive, and thus undesirable, but if correction were to take place only near then end of delivery then there would be a risk of over-delivery before the correction takes place. The present technique offers a good compromise between the two.

Figure 14:
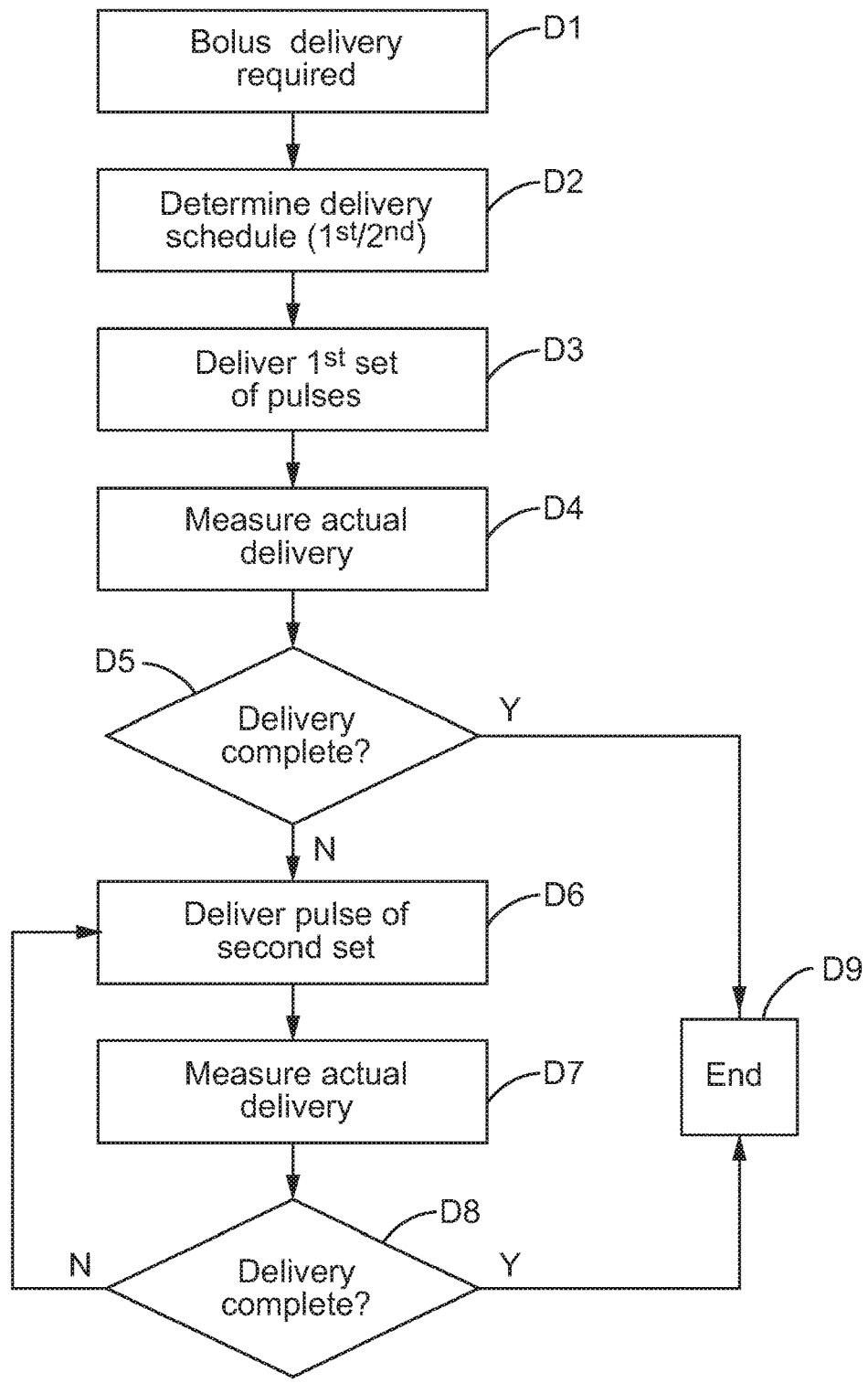
FIG. 14 is a schematic flow diagram for a second correction technique for bolus delivery.

Moreover, a second correction technique is used in conjunction with this (although the two techniques are each suitable for use individually), as illustrated in the schematic flow diagram of FIG. 14. In FIG. 14, a bolus delivery is required at a step D1. This bolus delivery could be the 50% delivery scheduled in the step C4 of FIG. 13, or it could be the remaining delivery amount of the step C3 of FIG. 13, or it could be a subset of either of these. For example, if a delivery schedule in FIG. 13 (e.g. for one of the steps C3 or C4) were to be required to deliver 2 units of insulin, then the correction technique of FIG. 14 could be applied for example to the delivery of a set of pulses for delivering one unit of insulin. In this case the technique of FIG. 14 could be applied twice—one for each unit of insulin to be delivered. At a step D2, a delivery schedule for a bolus delivery amount determined at the step D1 is calculated. The delivery schedule comprises a first set of pulses each of which delivers 0.1 units of insulin, followed by a second set of pulses each of which delivery 0.05 units of insulin. For example, the delivery schedule may comprise 8 long pulses (delivering 0.8 units in total) followed by four short pulses (delivering 0.2 units in total), giving an overall delivery of 1 unit of insulin. It will be appreciate that other combinations of long and short pulses could be used, and that the long and short pulses can be used in other embodiments to deliver amounts of insulin other than 0.1 units and 0.05 units. At a step D3, the first set of pulses are delivered. At a step D4, the amount of insulin actually delivered at the step D3 is measured, and this is compared, at a step D5, against the total amount of insulin intended to be delivered by way of the delivery schedule determined at the step D2, to identify whether delivery has been completed early. If at the step D5 it is determined that delivery is already complete, then at a step D9 the process is terminated (and may return to the step D1 if there is more insulin to be delivered by way of a further delivery schedule). If at the step D5 it is determined that delivery is not complete, then at a step D6 a pulse from the second set of (shorter) pulses is delivered, and then at a step D7 the amount of insulin actually delivered is measured. Then, at a step D8 the amount of insulin actually delivered (by the step D3 in combination with the step D6) is compared against the total amount of insulin intended to be delivered, to identify whether delivery has been completed early. If at the step D8 it is determined that delivery is already complete, then at a step D9 the process is terminated (and may return to the step D1 if there is more insulin to be delivered by way of a further delivery schedule). If at the step D8 it is determined that delivery is not complete, then the process returns to the step D6, where the next pulse in the second set of pulses is delivered. This process continues until either the delivery schedule determined at the step D2 completes, or until a determination is made at the step D8 that insulin delivery has completed ahead of schedule. It should be noted that this technique will not actually add pulses if under-delivery occurs. It will be appreciated that, while in the above example the set of pulses delivered before taking account of actual delivery is coincident with the set of longer pulses, this need not be the case. In some cases only some of the longer pulses may be delivered before actual delivery is taken into account (i.e. the process could be discontinued during the delivery of the longer pulses, not just during the delivery of the shorter pulses). In other cases the actual delivery may only be taken into account after some of the shorter pulses have already been delivered.

While embodiments of the present invention have been described with reference to an insulin delivery system, it will be appreciated that the present invention may be applied instead to the delivery of other drugs.

What is claimed is:

1. An actuator, comprising:
   a cavity containing a working medium that reversibly expands as it undergoes a phase change from a solid to a liquid state;
   a diaphragm disposed adjacent the cavity such that expansion and contraction of the expandable working medium causes the diaphragm to deflect;
   a semiconductor element disposed in the cavity, wherein the semiconductor element is operable in a first mode to heat the working medium to cause it to undergo the phase change into the liquid state, and is operable in a second mode to measure the temperature at the semiconductor element, wherein in the first mode, a first constant current is applied across the semiconductor element to heat the working medium, and in the second mode, a second constant current lower than the first constant current is applied across the semiconductor element, a voltage drop across the semiconductor element is measured, and the voltage drop is used to infer the temperature at the semiconductor element.

2. An actuator according to claim 1, wherein the semiconductor element is a diode.

3. An actuator according to claim 1, comprising control circuitry for setting a pulse start time and a pulse duration for applying an electric current to the semiconductor element, at least one of the pulse start time and pulse duration being set in dependence on the temperature measured by the semiconductor element.

4. An actuator according to claim 3, wherein the deflection of the diaphragm is used to pump a therapeutic product to a patient.

5. An actuator according to claim 4, wherein in a basal delivery mode, the control circuitry is operable to set the pulse duration in dependence on the temperature measured by the semiconductor element just before the pulse is due to be started.

6. An actuator according to claim 4, wherein in a bolus delivery mode, the control circuitry is operable to trigger the start of a new pulse when the temperature measured by the semiconductor element has dropped to a predetermined temperature following the end of the previous pulse.

7. An actuator according to claim 6, wherein the pulse duration of each new pulse is set in dependence on the predetermined temperature.

8. An actuator according to claim 5, wherein in the basal delivery mode, the control circuitry is operable to control the rate of delivery of the therapeutic product by setting the frequency with which pulses of electric current are applied to the semiconductor element.

9. An actuator according to claim 5, wherein in the basal delivery mode, the control circuitry is operable to monitor an amount of therapeutic product delivered over the previous n pulses, wherein n is an integer value greater than zero, and to modify a pulse parameter in relation to the next one or more pulses in dependence on a difference between an intended delivery quantity and an actual delivery quantity over those n pulses.

10. An actuator according to claim 9, wherein the pulse parameter is the duration of the next one or more pulses.

11. An actuator according to claim 9, wherein the pulse parameter is an interval between successive pulses.

12. An actuator according to claim 11, wherein if the actual delivery quantity is less than the intended delivery quantity then the duration of the next pulse is increased by an amount which is dependent on the magnitude of the difference, and if the actual delivery quantity is more than the intended delivery quantity then the duration of the next pulse is decreased by an amount which is dependent on the magnitude of the difference.

13. An actuator according to claim 6, wherein in the bolus delivery mode, the control circuitry is operable to deliver a predetermined bolus dose by calculating a first schedule of successive pulses required to deliver a first portion of the predetermined bolus dose, applying the calculated first schedule of successive pulses, determining an amount of therapeutic product delivered over the first schedule of successive pulses, calculating a second schedule of successive pulses required to deliver a next portion of the predetermined bolus dose in dependence on either a difference between an intended delivery quantity for the first portion and an actual delivery quantity delivered over the first schedule, or in dependence on an amount of therapeutic product still to be delivered, and applying the calculated second schedule of successive pulses.

14. An actuator according to claim 13, wherein the control circuitry is further operable to determining an amount of therapeutic product delivered over a previous schedule of successive pulses, calculate a further schedule of successive pulses required to deliver a next portion of the predetermined bolus dose in dependence on either a difference between an intended delivery quantity for the previous portion and an actual delivery quantity delivered over the previous schedule, or in dependence on an amount of therapeutic product still to be delivered, and applying the calculated further schedule of successive pulses.

15. An actuator according to claim 13, wherein the control circuitry is further operable to calculate a final schedule of successive pulses when the amount of therapeutic product remaining to be delivered is less than or equal to a predetermined amount.

16. An actuator according to claim 6, wherein in the bolus delivery mode, the control circuitry is operable to deliver a predetermined amount of therapeutic product by applying a schedule of successive pulses, wherein the control circuitry is responsive to a determination that the predetermined amount of therapeutic product has been delivered before the schedule of successive pulses has been completed to discontinue the delivery of pulses.

17. An actuator according to claim 16, wherein the schedule of successive pulses comprises a first set of pulses followed by a second set of pulses, each pulse in the first set of pulses having a longer duration than each pulse in the second set of pulses.

18. A therapeutic product delivery device comprising an actuator according to claim 1.

* * * * *